(12) United States Patent
McNally et al.

(10) Patent No.: US 6,391,049 B1
(45) Date of Patent: *May 21, 2002

(54) SOLID BIODEGRADABLE DEVICE FOR USE IN TISSUE REPAIR

(75) Inventors: Karen M. McNally, Plainfield, IN (US); Brian S. Sorg; Ashley J. Welch, both of Austin, TX (US)

(73) Assignee: Board of Regents the University of Texas System, Austin, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/413,604

(22) Filed: Oct. 6, 1999

(51) Int. Cl.$^7$ ................................................ A61B 17/08
(52) U.S. Cl. ....................................................... 606/214
(58) Field of Search ................................ 606/212, 213, 606/214, 215, 8, 40, 154, 7; 623/1.41

(56) References Cited

U.S. PATENT DOCUMENTS

| | | | |
|---|---|---|---|
| 4,411,027 A | 10/1983 | Alexander et al. .................. 3/1 |
| 4,804,691 A | 2/1989 | English et al. ............... 523/118 |
| 4,854,320 A | 8/1989 | Dew et al. .................. 128/397 |
| 4,895,148 A | 1/1990 | Bays et al. .................. 606/213 |
| 5,002,051 A | 3/1991 | Dew et al. ................... 128/395 |
| 5,085,861 A | 2/1992 | Gerhart et al. ............ 424/78.17 |
| 5,118,293 A | * 6/1992 | Levy ........................... 433/215 |
| 5,290,272 A | 3/1994 | Burstein et al. ................ 606/4 |
| 5,292,362 A | 3/1994 | Bass et al. .................. 106/124 |
| 5,507,744 A | 4/1996 | Tay et al. ...................... 606/50 |
| 5,571,216 A | 11/1996 | Anderson ..................... 623/66 |
| 5,612,050 A | 3/1997 | Rowe et al. ................. 424/423 |
| 5,669,934 A | 9/1997 | Sawyer ........................ 606/213 |
| 5,686,091 A | * 11/1997 | Leong et al. ................ 606/213 |
| 5,713,374 A | 2/1998 | Pachence et al. ............ 128/898 |
| 5,713,891 A | 2/1998 | Poppas ........................... 606/2 |
| 5,749,895 A | * 5/1998 | Sawyer et al. .............. 606/214 |
| 5,770,417 A | 6/1998 | Vacanti et al. .............. 435/180 |
| 5,810,810 A | 9/1998 | Tay et al. ...................... 606/50 |
| 5,824,015 A | 10/1998 | Sawyer ........................ 606/214 |
| 5,855,610 A | 1/1999 | Vacanti et al. ................. 623/11 |
| 5,879,359 A | 3/1999 | Dorigatti et al. ............. 606/152 |
| 6,087,552 A | * 7/2000 | Gregory ......................... 623/1 |

\* cited by examiner

Primary Examiner—Michael J. Milano
Assistant Examiner—Vy Q. Bui
(74) Attorney, Agent, or Firm—Santa E. Warren, Jr.; Edwin S. Flores; Gardere Wynne Sewell LLP (57) ABSTRACT

A composition and method for a light activated composition for improved wound closure, is disclosed. The composition includes a biodegradable polymer that is impregnated with a solder that is biologically compatible and a chromophoric dye. The chromophoric dye enhances the amount of light energy that the composition absorbs.

21 Claims, 6 Drawing Sheets

SOLID BIODEGRADABLE DEVICE FOR USE IN TISSUE REPAIR

TECHNICAL FIELD OF THE INVENTION

The present invention relates in general to the field of biological tissue repair. More particularly, it concerns a new light activated device, which can be used for improved wound closure.

BACKGROUND OF THE INVENTION

The conventional methods for tissue repair use sutures, staples or clips [Werker 1997]. Sutures are favored because they are cost effective, reliable and more importantly, are suitable for almost any type of tissue. The use of any of these conventional fasteners, however, causes tissue injury due to their mechanical intrusion. By their very nature, they result in a "foreign body" being left in the tissue. Tissue injury and foreign body reaction can give rise to such problems as inflammation, granuloma formation, scarring, and stenosis. Sutures become difficult or tedious to execute in microsurgical or minimally invasive endoscopic applications, where staples or clips are better suited. Staples and clips are not easily adapted to different tissue dimensions, however, and maintaining precision of alignment of the tissue is difficult because of the relatively large force required to fit them. Finally, none of these fasteners produce a watertight seal over the repair.

Laser welding is another technique used to achieve tissue anastomosis. Laser energy is used to induce thermal changes in connective tissue proteins. As temperatures rise and/or heating times are prolonged, cellular and tissue structural proteins undergo denaturation and conformational changes, a process defined as coagulation [Pearce 1995]. This process results in the joining or bonding of the adjoining tissue edges [Schober 1986, Bass 1992]. A wide range of lasers have been used for laser tissue welding. Infrared sources include carbon dioxide ($CO_2$), thulium-holmium-chromium, holmium, thulium and neodymium rare earth doped garnets (THC:YAG,Ho:YAG, Tm:YAG or Nd:YAG), and gallium aluminium arsenide diode (GaAlAs) lasers. Visible sources include potassium-titanyl-phosphate (KTP) frequency-doubled Nd:YAG and argon lasers. The laser energy is absorbed by water at the infrared wavelengths and by hemoglobin and melanin at the visible wavelengths, thereby heating proteins within the target tissue.

Compared with conventional tissue repair techniques, the laser welding technique offers reduced suture and needle trauma [Godlewski 1996], reduced foreign body reaction [Dalsing 1992], reduced bleeding [Chikamatsu 1995], the potential to form an immediate watertight anastomosis intra-operatively [Bass 1995] and shorter operating times [Maragh 1988]. While some success has been achieved in experimental applications, clinical use of this technology has been hindered by unreliable fusion strength [Jain 1979, Grubbs 1988], excessive thermal damage of tissue caused by direct laser heating [Thomsen 1985, Kopchok 1988, Chow 1990], technical difficulties with tissue alignment [Bass 1995], the ambiguity of the end point for the procedure [Bass 1995], and by poor reproducibility [Thomsen 1995].

Laser soldering using protein based biological glues and other compounds is another tissue repair technique that may provide greater bond strength and lesser collateral thermal damage with a greater tolerance of variations in laser parameters. Useful solders include blood [Krueger 1985, Wang 1988], cryoprecipitate [Grubbs 1988, Cikrit 1990], and albumin [Poppas 1988, Bass 1993, Poppas 1993]. Wavelength-specific chromophores (dyes) are often added to the solders to provide for differential absorption between the dyed region and the surrounding tissue. One advantage of the laser soldering technique is that the area may be bathed by the laser radiation while energy is absorbed selectively only by the target. Hence, the requirement for precise focussing and aiming of the laser beam may be removed. Furthermore, due to the increased absorption characteristics of the dyed tissue, lower laser irradiances may be used to achieve the required effect, and thus, the safety of the technique is increased. Examples of such dyes include carbon black, Fen 6, indocyanine green and fluorescein.

SUMMARY OF THE INVENTION

The use of synthetic polymers as a scaffold for protein solders provides a new device, which may be tailored to a wide range of clinically relevant geometries for tissue repair. The features of the novel solder-doped polymeric scaffolds of the present invention greatly improve the clinical applicability of laser tissue repair. For example, problems associated with inflexibility in conforming to various tissue geometries, instability in a hydrated environment due to non-uniform tissue adhesive denaturation, and solubility in physiological fluids prior to denaturation are overcome using the new materials of this invention. The materials and methods described herein offer a viable alternative to conventional fasteners, including sutures, staples and clips, currently used for tissue repair. In addition, the present invention permits the use of patches prepared from the solder-doped polymeric scaffolds in the field, thereby providing a simple and effective method to stop bleeding and repair tissue quickly in an emergency situation.

Polymer scaffolds are fabricated with synthetic materials including, but not limited to, poly(L-lactic acid) (PLA), poly(glycolic acid) (PGA), poly(L-lactic-co-glycolic acid) PLGA, poly(.epsilon.-caprolactone), polyortho esters, polyanhydrides and poly glycerol (PEG), using a solvent-casting and particulate-leaching technique. The scaffold forms a platform for the protein solder that is composed of such materials as, but not limited to, serum albumin, collagen and fibrinogen. A chromophoric dye such as indocyanine green (ICG) or carbon black may be added to the solder to selectively absorb the laser irradiation. The end result is a device, which can be light activated and used to join tissue together.

The polymeric scaffold described herein is designed to mimic the body's own extracellular matrix [Mikos 1994]. Furthermore, the present invention provides a porous network into which traditional protein solders are readily absorbed, and degrades as need for the support diminishes. The solder, the polymer scaffolds and the chromophoric dye are biocompatible, and thus, foreign body reaction and infection are expected to be minimal. In fact, polylactic acid-based polymers are commercially available, and already have FDA approval for clinical procedures. Upon activation with a laser, the solder-doped scaffolds tend to undergo a small amount of shrinkage. This shrinkage helps to maintain edge-alignment as the tissue edges are gently pulled together. In addition, slight-rehydration of the solder-doped polymer scaffolds upon application to the tissue assists with tissue apposition, thus relieving the need for excessive stay-sutures often associated with laser tissue repair techniques. Various dopants including, hemostatic and thrombogenic agents, antibiotics, anesthetics, and various growth factors may be added to the solder-doped polymer scaffolds to assist in the wound healing process.

The present inventors recognized that there are three primary disadvantages of previously described solders.

Figure 1:
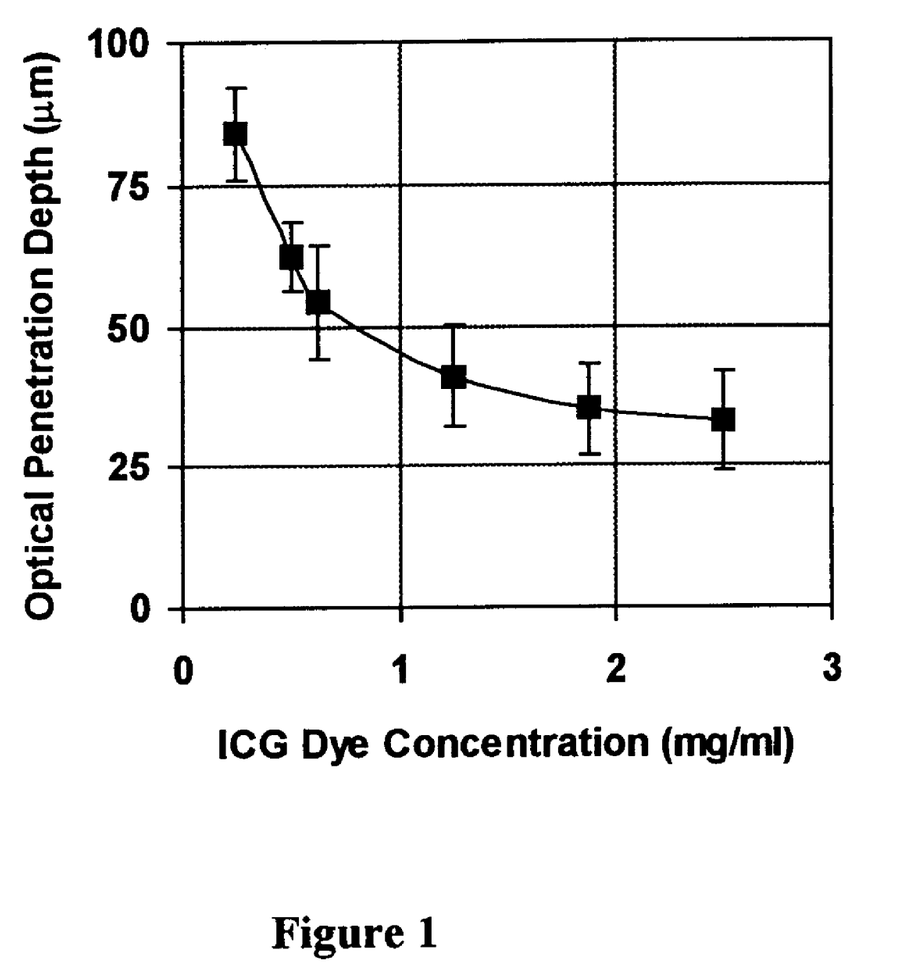
FIG. 1. Optical penetration depth of 805 nm light in solid protein solders (60% BSA) at a range of indocyanine green (ICG) dye concentrations. Each point represents the mean and standard deviation from measurements made on three specimens. The optical penetration depth is observed to decrease with increased ICG dye concentration.

First, application of such solders to the repair site can be difficult. Liquid protein solders suffer from problems associated with "runaway" of the low viscosity material [McNally 1999a, McNally 1999b, McNally 1999e]. Solid protein solders, while offering improved repair strength over liquid solders, are brittle and inflexible, and thus, not easily adapted to different tissue geometries [McNally 1999d, McNally 1999e, McNally 1999f]. Second, more energy is generally absorbed near the upper portion of the solder, which is closer to the laser source, regardless of whether water or an absorbing dye is used as the chromophore. Irradiation of the solder produces a temperature gradient over the depth of the solder. The gradient is a function of the irradiance and the absorption coefficient, $\mu_a$, of the solder/dye combination. The 1/e penetration depth of the laser light is defined as $1/\mu_a$, neglecting scattering. FIG. 1 shows a plot of the optical penetration depth of laser light at 805 nm in albumin protein solders containing different concentrations of ICG dye. The optical penetration depth is observed to decrease with increased ICG dye concentration. Depending on the temperature gradient and the laser exposure, the upper portion of the solder can become over-coagulated while the most critical region—the solder/tissue interface—remains uncoagulated. Non-uniform denaturation across the solder thickness can result in the formation of an unstable solder-tissue bond [McNally 1999b, Chan 1997]. Third, the protein solder is soluble in physiological solutions prior to laser irradiation, which can be problematic during application. In addition, as these solders are often subjected to blood dilution during operation, the solder may undergo mechanical alteration that can weaken the solder-tissue repair [Lauto 1998].

More particularly, the present invention includes a composition suitable for the repair of separated biological tissue using a biodegradable polymer that is impregnated with a solder that is biologically compatible and a chromophoric dye that enhances the amount of light energy that the composition will absorb.

The present invention also includes a method for the application of the biodegradable polymer containing the weldable material and chromophoric dye to biological tissue and affixing it there by application of laser light. The steps in the method are placing the pieces of separated biological tissue, if they are completely separated, in proximity close to one another approximating their normal relationship with one another; placing the polymeric biodegradable scaffold containing the solder material and the chromophoric dye over, around or in the wound of the biological tissue in a manner that will allow the wound to be sealed after the composition is exposed to laser light; and exposing the polymeric material containing the solder and the chromophoric dye to a laser light in order to cause the adhesion of the solder and the polymer scaffold to the biological tissue.

In summary, the present invention includes a composition suitable for the repair of separated biological tissue using a biodegradable polymer that is impregnated with a solder that is biologically compatible and a chromophoric dye that enhances the amount of light energy that the composition will absorb.

BRIEF DESCRIPTION OF THE DRAWINGS

While the making and using of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and do not delimit the scope of the invention.

DETAILED DESCRIPTION OF THE INVENTION

While the making and using of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and do not delimit the scope of the invention. In particular, the detailed description and discussion of the preparation steps for the various embodiments of the present invention in Examples 1 to 4 are not intended to limit the scope of the invention.

Solder-doped polymer scaffolds have been developed as an alternative to conventional fasteners and traditional protein solders for tissue repair. The new scaffolds offer flexibility along with improved repair strength over previous published results using albumin protein solders alone [McNally 1999a, McNally 1999b, McNally 1999c]. The properties of the solder-doped scaffolds can be easily tailored to meet the specific requirements of a wide range of clinical applications. The new scaffolds provide a quick and easy method of joining tissue in surgery.

Preparation of ICG-Doped Albumin Protein Solders

Liquid protein solder was prepared from either 25%(w/v) or 50%(w/v) bovine serum albumin (BSA) (Cohn Fraction V, Sigma Chemical Company, St. Louis, Mo.) and indocyanine green (ICG) dye (Sigma Chemical Company, St. Louis, Mo.) at a concentration of 0.5 mg/ml, mixed in deionized water. The solder was stored in a light-proof plastic vials at 4° C. until required.

Solid protein solder was prepared from 60%(w/v) BSA and ICG dye at a concentration of 0.5 mg/ml, mixed in deionized water. The mixture was pressed to a thickness of 0.15±0.01 mm and then cut into rectangular strips of the desired surface area and allowed to dry. The solid protein solder strips were stored in a light proof container between two inert metal plates at 4° C. until required.

Preparation of Solder-Doped PLGA Polymer Scaffolds

Porous synthetic polymer scaffolds were prepared using poly(L-lactic-co-glycolic acid) (PLGA) with a lactic:glycolic acid ratio of 85:15 and 70% weight fraction sodium chloride using a solvent-casting and particulate leaching technique [Mikos 1993]. For example, 200 mg PLGA (Sigma Chemical Company, St. Louis, Mo.) were dissolved in 2 ml dichloromethane (Sigma Chemical Company, St. Louis, Mo.) and then combined with 467 mg NaCl of the desired particle size. Two salt particle size ranges were used: ≦106 µm and 106–150 µm. These particle sizes were obtained by grinding the salt particles with a mortar and pestle and then sifting them through No. 100 and No. 140 sieves (VWR Scientific, South Plainfield, N.J.). The scaffolds were cast into 60 mm diameter petri dishes and left in a fume hood for 24 hours to allow the dichloromethane to evaporate. The salt was leached out of the scaffolds by immersion in filtered deionized water for 24 hours. During the leach-out period the water was changed 3–4 times. The scaffolds were then air-dried and stored at room temperature until required.

After air drying, the PLGA scaffolds were cut into strips of the desired surface area and left to soak for two hours in the liquid protein solder (either 25%(w/v) or 50%(w/v) BSA). Before use, the solder-doped polymer scaffolds were left to dry for approximately 60 s on a piece of parafilm. The average thickness of the solder-doped polymer scaffolds, determined by scanning electron microscopy (Philips 515, Holland) and measurement with precision calipers (L.S. Starrett Co., Anthol, Mass.), was 202±12 µm.

Biodegradability

The solder, the polymer scaffolds and the chromophoric dye are all bio-compatible. Foreign body reaction is expected to be minimal using the new device as the degradation products of the scaffolds, including lactic acid and glycolic acid for the example of PLGA scaffolds, are naturally occurring substances inside the body [Wake 1996]. Altering the macromolecular structure of the scaffold may also control the degradation rate of the scaffolds. For example, the degradation rate of the scaffolds may be altered from days to years by varying the ratio of polylactic acid (PLA) to polyglycolic acid (PGA) and may be varied from 0 to 100% in PLGA scaffolds.

Any suitable bio-compatible polymers, solders and chromophoric dyes may be used to prepare the solder-doped polymeric scaffolds. Suitable examples of polymers include poly(L-lactic acid) (PLA), poly(glycolic acid) (PGA), poly (L-lactic-co-glycolic acid) PLGA, poly(.epsilon.-caprolactone), polyortho esters, polyanhydrides and the like. Suitable examples of protein solders include serum albumin, collagen and fibrinogen. Suitable examples of chromophoric dyes include water, indocyanine green (ICG) and carbon.

Porosity

The polymer scaffolds are porous. The porosity of the scaffolds is easily controlled by, for example, altering the salt (e.g., sodium chloride) weight fraction and salt particle size used during the casting stage of the scaffolds. By using salt particles of different sizes, scaffolds can be prepared with various porosities. The synthetic polymer scaffolds were prepared using 100 mg of PLGA with a lactic:glycolic acid ratio of 85:15 and 70% weight fraction NaCl. Scaffolds were prepared with two salt particle sizes: ≦106 µm and 106 to 150 µm. By using salt particles of different sizes, scaffolds were prepared with the same porosity but with different pore diameters.

Figure 2:
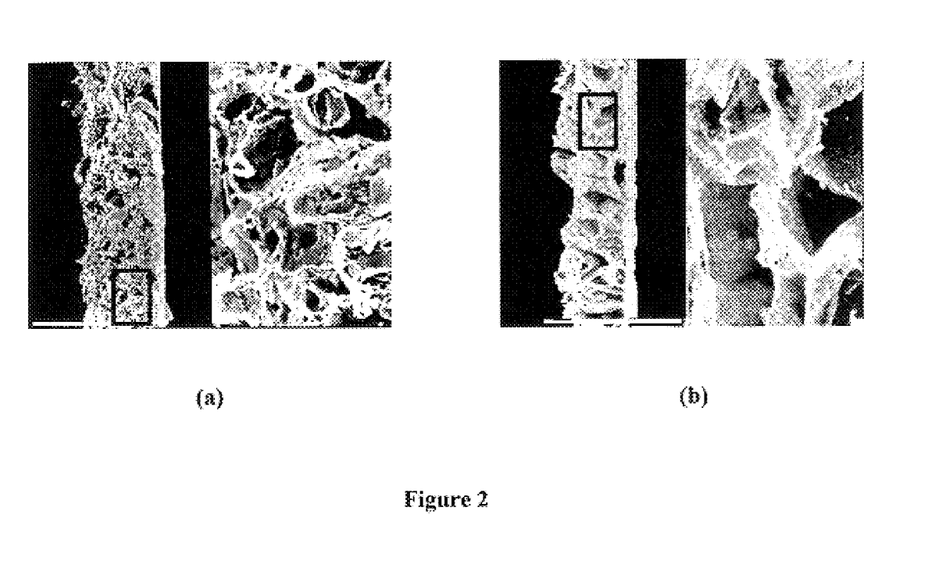
FIG. 2. Scanning electron micrographs of examples of the synthetic polymer scaffolds prepared with two salt particle sizes.

FIG. 2a shows an example of a scaffold cast using salt particle sizes ≦106 µm in diameter. FIG. 2b shows an example of a scaffold cast using salt particle sizes of 106 to 150 µm in diameter. The right half of each micrograph shows a higher magnification view (526×) of the section of the micrograph highlighted by a rectangular frame on the left half of the micrograph (88×). The scaffolds exhibit a uniform pore morphology, which is interconnected, thus yielding an open-cell polymer.

Figure 3:
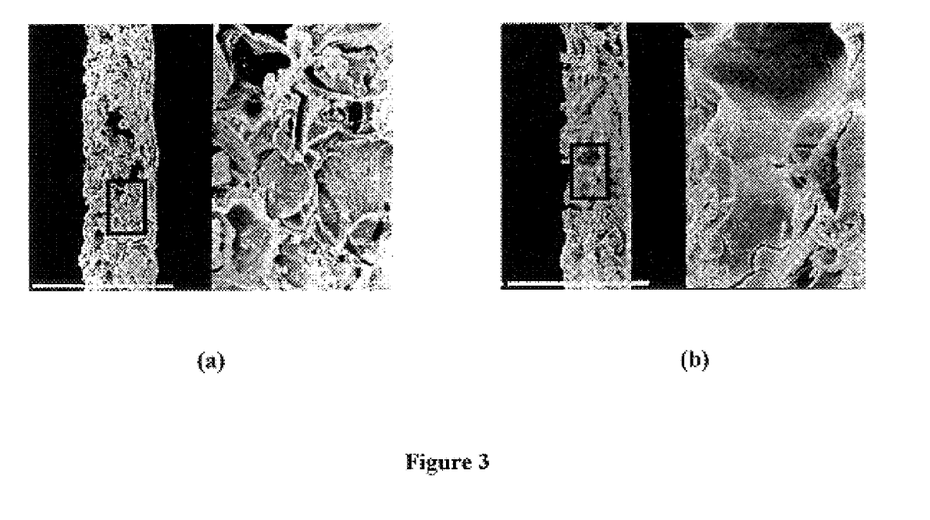
FIG. 3. Scanning electron micrographs of examples of the solder-doped polymer scaffolds with Bovine Serum Albumin.

FIGS. 3a and 3b are scanning electron micrographs of the solder-doped polymer (PLGA) scaffolds formed with 25% BSA and the two salt particle sizes. The solder-doped polymer scaffolds were prepared using solders composed of 25% BSA and polymers prepared from 100 mg of PLGA with a lactic:glycolic acid ratio of 85:15 and 70% weight fraction NaCl. Scaffolds were prepared with two salt particle sizes: (a)≦106 µm and (b) 106 to 150 µm. Original magnification of micrographs—3a: 88×; 3(b): 526×. The scaffolds exhibit a uniform pore morphology, which is interconnected, thus yielding an open-cell polymer. Many of the pores of the scaffolds formed with salt particles ≦106 µm in diameter remained unfilled (FIG. 3a). The albumin protein solders appeared to be better able to permeate the polymer scaffold containing the larger pore diameters (FIG. 3b).

Flexibility and Three-Dimensional Shaping

Pliability is an important consideration, particularly for blood vessels and intestines that require a tubular scaffold. Other non-tubular soft tissues such as skin also require a flexible matrix that can conform to a variety of different contours.

Figure 4:
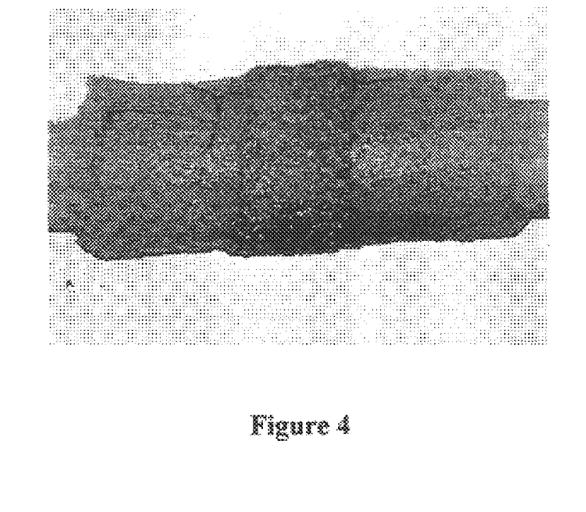
FIG. 4. A photograph showing that the solder-doped polymer scaffolds are pliable and elastic and thus it is easy to process and fabricate them into different forms and shapes.
Figure 5:
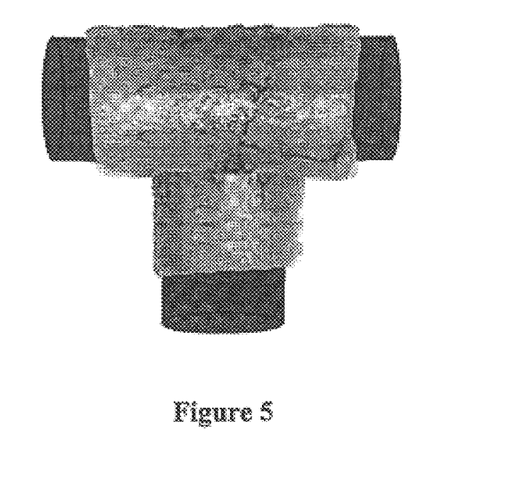
FIG. 5. A photograph showing that it is possible to mold the solder-doped polymer scaffolds of the present invention into a range of different clinically relevant geometries. A schematic of a T-mold for end-to-side vascular anastomosis is shown.

FIGS. 4 and 5 demonstrate the flexible nature of the scaffolds are evidenced by their ability to wrap around a canine carotid artery (FIG. 4) and a T-shaped junction (FIG. 5). In FIG. 4, the scaffold is formed without macroscopic damage to the scaffold. The solder used in FIG. 4 was composed of 50% bovine serum albumin (BSA), 0.5 mg/ml indocyanine green (ICG) and deionized water, and the polymer scaffold was formed using 100 mg poly(lactic-co-glycolic acid) (PLGA) and 70 wt % NaCl (salt particle size 106 to 150 μm). The scaffolds are pliable and elastic and thus it is easy to process and fabricate them into different forms and shapes. Another method for increasing the flexibility of the scaffolds is to add poly glycerol (PEG) to the polymer mixture during the casting stage.

Tubular scaffolds have been prepared using the solder-doped polymer scaffolds. The PLGA scaffolds were prepared as described above with 100 mg PLGA and 70 wt % NaCl (salt particle size 106 to 150 μm), and cut into rectangular sections approximately 1 cm long and 0.75 cm wide. The scaffold was rolled into a tube and the ends of the tube were sealed by slightly dissolving the edges with chloroform and pressing them together for approximately 15 s [Wake 1996]. The resulting tubular structures were approximately 2 mm in diameter and had a wall thickness of approximately 150 μm. The scaffolds were soaked in albumin protein solder for a period of two hours and allowed to dry on parafilm afterwards. The final wall thickness of the solder-doped tubular scaffolds was approximately 200 μm. As shown in FIG. 5, development of new molds to create set scaffold geometries suitable to various clinical applications, such as a T-mold for end-to-side vascular anastomosis, are possible.

Doping with Therapeutic Agents

Various therapeutically effective dopants including but not limited to hemostatic and thrombogenic agents, antibiotics, anesthetics, various growth factors, enzymes, antiflammatories, bacteriostatic or bacteriocidal factors, chemotherapeutic agents, anti-angiogenic agents and vitamins can be added to the solder-doped polymer scaffolds. Controlled release of these agents can assist in the wound healing process.

Additional Features

The presence of the solder coagulum increases the initial strength of the repair, while the presence of the chromophoric dye provides for selective absorption of the laser light. As tissue absorption at a laser wavelength of approximately 800 nm is low, the dyed solder absorbs most of the incident light energy. Consequently, the amount of collateral tissue thermal damage due to direct absorption of the laser light is minimized. Besides exogenous chromophores added to the solder, water and natural chromophores of the solder-doped polymer scaffold can be used to absorb laser light.

Slight rehydration of the solder-doped polymer scaffolds upon application to the tissue assists with tissue apposition, thus relieving the need for excessive stay-sutures, often associated with laser tissue repair techniques. In addition, upon activation with a laser, the solder-doped polymer scaffolds tend to undergo a small amount of shrinkage. This shrinkage helps to maintain edge-alignment as the tissue edges are gently pulled together. In addition, contrary to conventional suturing, the solder-doped polymer scaffolds can provide an immediate leak-free closure.

Polymeric Scaffolds Containing a Concentration Gradient of Chromophoric Dye

Instead of using a polymer scaffold saturated with a single concentration of the chromophoric dye, two different scaffolds saturated with two different concentrations of dye may be used to produce a single unit with a gradient of dye concentration across its thickness. For example, two solder-doped polymer scaffolds, containing different dye concentrations, are pressed together using a vice to form a single solid scaffold. The two scaffolds are pressed together immediately after preparation and prior to drying so as to create a chromophore concentration gradient across the thickness of the scaffold, rather than two separate layers.

Reduced Solubility in Physiological Solutions

The protein solder is soluble in physiological solutions prior to laser irradiation, which can be problematic during application. In addition, as these solders are often subjected to blood dilution during operation, the solder may undergo mechanical alteration that can weaken the solder-tissue repair [Lauto 1998]. Predenaturation of the solder-doped polymer scaffolds reduces the solubility of the scaffolds in a fluid environment prior to denaturation. Two such methods of predenaturation may include soaking the scaffolds in a hot water bath at a temperature of 70 to 80 C., or tanning with glutaraldehyde. Tanning with glutaraldehyde has previously been applied to human umbilical vein grafts [How 1992], collagen grafts prepared from bovine carotid arteries [Rosenberg 1982] and albumin coated knitted polyester grafts [Kottke-Marchant 1989], to improve the tensile strength of the grafts.

EXAMPLE 1

In vitro Tissue Soldering of Bovine Thoracic Aorta

Biodegradable polymer films of controlled porosity were fabricated with poly(L-lactic-co-glycolic acid) (PLGA) and poly(ethylene glycol) (PEG) using a solvent-casting and particulate-leaching technique. The porous films provided a scaffold into which the traditional protein solder composition of bovine serum albumin (BSA) and indocyanine green (ICG) dye mixed in deionized water was readily absorbed. Studies were conducted to assess the influence of various processing parameters on the strength of tissue repairs formed using the new scaffolds. These parameters included the PLGA copolymer ratio, the PLGA/PEG blend ratio, the initial salt weight fraction, the salt particle size, and the initial albumin weight fraction.

Bovine thoracic aortas were obtained from a slaughterhouse (Taylor Meat Company, Taylor, Tex.). The aortas were rinsed with phosphate-buffered saline to remove blood from the tissue surface. A full thickness incision was cut through the specimen width using a scalpel and the severed ends were placed together. Laser soldering was performed on the intima side of the aorta. The solder-doped polymer scaffold was placed perpendicularly across the junction of the severed aorta specimen and then denatured with a continuous pass of the diode laser output.

A GaAlAs semiconductor diode with a nominal output power of 5 W and wavelength of 805 nm (Opto Power Corp., Tucson, Ariz.) was used to denature the scaffold. The laser light was coupled into a 660 μm diameter silica fiber bundle and focussed onto the scaffold surface with an imaging hand-piece connected at the end of the fiber. The diode was operated in continuous mode with a l/e spot size at the scaffold surface of 1.5 mm. Irradiances of 5.7, 11.3 and 17.0 W/cm$^2$, measured using a Molectron EPM 2000e power meter with a PM30 thermopile detector (Molectron Detector, Inc., Portland, Oreg.), were delivered to the scaffold surface. The laser beam was scanned linearly across the length of the solder-doped polymer scaffolds four times (starting from one end) at a constant speed of 0.3 mm/s using a motorized stage (Oriel Corp., Stratford, Conn.) to move the specimen. The total exposure time for each solder-doped polymer scaffold was 40 s.

Alteration of the PLGA copolymer ratio had little effect on the strength of the repairs. Repair strength increased significantly with an increase in the size and number of pores present in the scaffolds and with increased BSA concentration. At the highest irradiance tested of 17.0 W/cm$^2$, the strength of repairs formed with the solder-doped polymer scaffolds was significantly improved over past results achieved using traditional solid protein solders (92.1±4.9 g [McNally 1999a]). In addition, the strength of repairs formed using the solder-doped scaffolds denatured at 17.0 W/cm$^2$ compared favorably with the strength of native aorta (91.2±4.7 g [McNally 1999 a]). In all cases, the solder-doped scaffold remained intact and pulled away from the tissue. In many instances a portion of the tissue was observed to remain bonded to the scaffold. Finally, the addition of PEG to the films during the casting stage was observed to increase the flexibility of the scaffolds.

EXAMPLE 2

In vivo Laser-assisted Vascular Fusion Using New Solder-doped Polymer Scaffolds The newly developed solder-doped polymer scaffolds were used as a substitute to traditional tissue solders for laser-assisted vascular tissue fusion without the need for sutures. Canine femoral arteries (n=8), femoral veins (n=8) and carotid arteries (n=8) were exposed, and a 0.8 cm longitudinal incision was made in the vessels. A solid laser activated adhesive material composed of poly(L-lactic-co-glycolic acid) and bovine serum albumin was used to close the incisions in conjunction with an 805 nm diode laser. Blood flow was restored to the vessel immediately after the procedure and the incision site was checked for patency. The new scaffolds were flexible enough to be wrapped around the vessel while their solid nature avoided the problems associated with "runaway" of the less viscous liquid protein solders currently used by researchers. Assessment parameters included measurement of the intraluminal bursting pressure one hour after surgery, as well as histology. A control study was also performed on canine femoral arteries and veins (n=4) using four to six sutures evenly spaced around the vessel wall. The acute intraluminal bursting pressures were significantly higher in the laser-solder group (>350 mmHg) compared to the suture group (<150 mmHg). Histological analysis showed no evidence of thrombosis formation in the laser-solder repair group. These initial results indicated that laser-assisted vascular repair using the new scaffolds is safe, easy to perform, and contrary to conventional suturing, provides an immediate leak-free closure. In addition, the flexible and moldable nature of the new scaffolds allows them to be tailored to a wide range of tissue geometries, thus greatly improving the clinical applicability of laser-assisted tissue repair.

EXAMPLE 3

In vivo Repair of Canine Ureters Using Solder-doped Polymer Scaffolds

Laser welding of the genitourinary tract has the potential advantage of forming an immediate watertight seal. In addition, it may obviate the need for sutures, eliminate foreign body reaction to sutures, and potentially improve healing. The feasibility of using the solder-doped polymer scaffolds for uretal repair was investigated using a canine model. Eight canine ureters were exposed, and a 0.8 cm longitudinal incision was made in the tube. The incision was repaired using a strip of the solder-doped polymer scaffold in conjunction with an ~800 nm diode laser. The dimensions of the strip were approximately 1.2×0.4×0.15 mm. Following the repairs the intraluminal bursting strength of each ureter was measured. Successful ureteral repairs were achieved in all solder groups while maintaining ureteral continuity at supraphysiologic pressures.

EXAMPLE 4

Novel Solid Protein Solder Designs for Laser-assisted Tissue Repair

Rectangular solid solder strips composed of indocyanine green (ICG)—doped albumin protein solders were used in conjunction with an 808 nm-diode laser. These investigations are furthered by in vitro studies conducted to assess a range of specially designed chromophore-enhanced solid protein solders manufactured and tested for application during laser-assisted anastomosis of bovine vascular specimens.

The study was divided into two parts. In the first part of the study, the creation of a chromophore concentration gradient across the thickness of the solder was investigated as a means to allow control of the heat source gradient through the solder. Increased deposition of the laser energy near the vital solder/tissue interface was achieved. In the second part of the study, predenaturation of the solid solder was investigated as a means for increasing the flexibility and decreasing the brittle nature of the solid solder. The resulting solder was flexible enough to be wrapped around the tissue while its solid nature avoided the problems associated with "runaway" of the less viscous liquid solders currently used by researchers. In addition, predenaturing the solder enhanced its stability in a hydrated environment thus improving the handling characteristics of the solder for clinical application.

Concentration Gradient of Chromophoric Dye

The creation of a chromophoric concentration gradient across the thickness of the solder was achieved by placing two solid protein solder strips, 75 $\mu$m in thickness, containing different ICG dye concentrations directly on top of each other, and pressing them together using a vice to form a single solid solder strip 150 $\mu$m in thickness. The solder strips were pressed together immediately after preparation, prior to drying, so as to create a chromophore concentration gradient across the thickness of the solder, rather than two separate layers. Four combinations of chromophore concentrations were used: 2.5 mg/ml:0.25 mg/ml, 1.875 mg/ml:0.625 mg/ml, 0.625 mg/ml: 1.875 mg/ml and 0.25 mg/ml:2.5 mg/ml. Solder strips containing 2.5 mg/ml ICG and 0.25 mg/ml ICG without the chromophore concentration gradient were also investigated.

Figure 6:
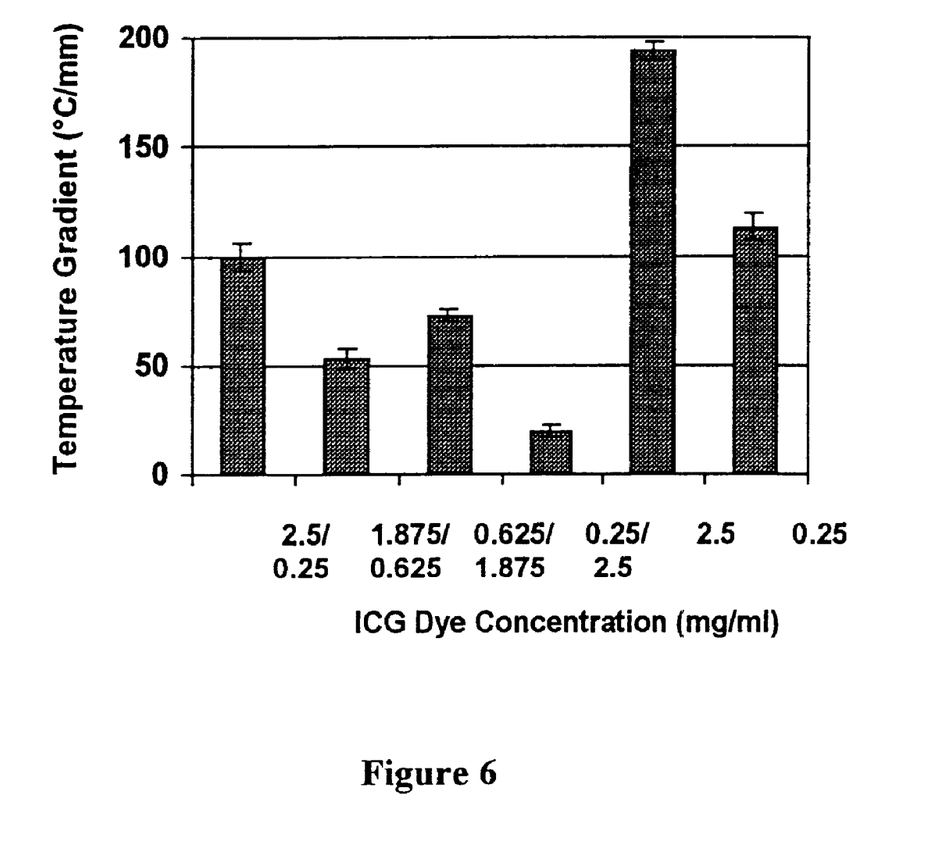
FIG. 6. A graph showing the temperature gradient across solid protein solder strips containing a range of ICG dye concentration gradients is shown.

FIG. 6 is a graph that shows the results of studies conducted to determine the total temperature gradient across the solid protein solder strips containing the various ICG dye concentration gradients. Results from measurements made on the four combinations of chromophore concentration gradients investigated (2.5 mg/ml:0.25 mg/ml, 1.875 mg/ml:0.625 mg/ml, 0.625 mg/ml:1.875 mg/ml and 0.25 mg/ml:2.5 mg/ml), and protein solders containing 2.5 mg/ml ICG and 0.25 mg/ml ICG without the chromophore concentration gradient, are presented. While the solid protein solder containing ICG dye concentrations of 2.5 mg/ml and 0.25 mg/ml produced an average temperature gradient across the solder of 193° C./mm and 113° C./mm, respectively, the temperature gradient was only 20° C./mm, using solder formed with a chromophore concentration gradient of 0.25 mg/ml:2.5 mg/ml ICG.

Figure 7:
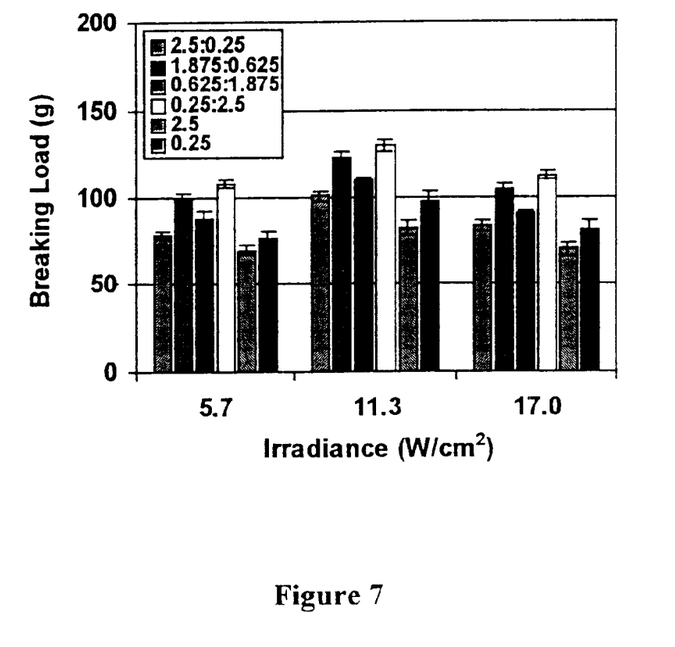
FIG. 7. A graph showing the breaking load of tissue specimens repaired using the solid protein solder strips (60% BSA) prepared with a range of ICG dye concentration gradients, as a function of laser irradiance. Each bar represents the mean and standard deviation for ten repairs.

FIG. 7 is a graph that shows the results of strength measurements made on tissue specimens successfully repaired using the solid protein solder strips prepared with a range of ICG dye concentration gradients, as a function of laser irradiance. The repair strength for each value of laser irradiance was calculated from the mean for ten repairs. The standard deviation is also shown in each case. Repairs formed with solders containing a chromophore concentration gradient of 0.25 mg/ml:2.5 mg/ml ICG were approximately 58% stronger than those formed using solder containing 2.5 mg/ml ICG, the most common ICG concentration used by researchers for laser tissue solder repair, and approximately 33% stronger than those formed using solder containing 0.25 mg/ml ICG.

Reduced Solubility in Physiological Solutions

Two methods of predenaturation of the solid protein solder strips (60% BSA) were investigated. The first method involved soaking the solder strips in a hot water bath at set temperatures of either 75° C. or 90° C. for approximately 30 s. The second method involved soaking the solder strips in glutaraldehyde at concentrations of 0.5 to 1.0% for approximately 30 s.

Figure 8A:
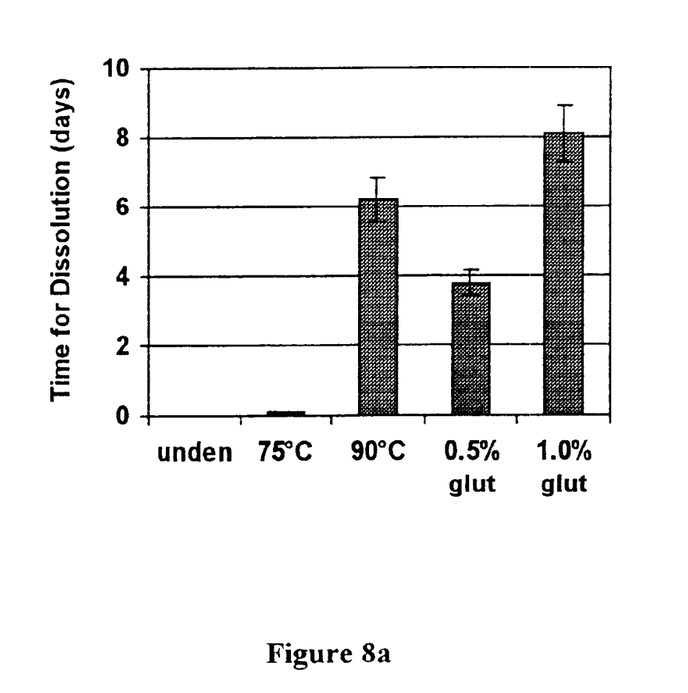
FIG. 8a. A graph that shows the time for dissolution in PBS of predenatured solid protein solder strips prior to laser irradiation. The time for dissolution for each group of solder was calculated from the mean for ten specimens. The standard deviation is also shown in each case.
Figure 8B:
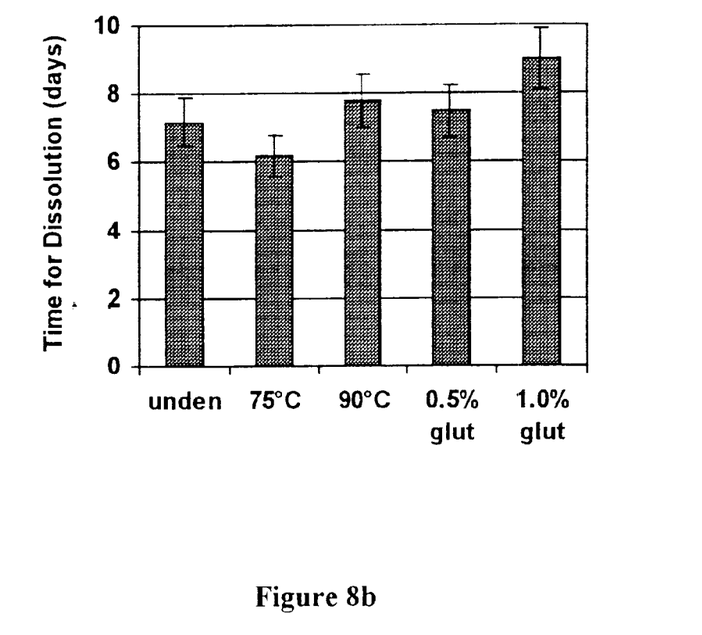
FIG. 8b. A graph that shows the time for dissolution in PBS of predenatured solid protein solder strips after laser irradiation at 11.3 W/cm$^2$ for 40 s. The time for dissolution for each group of solder was calculated from the mean for ten specimens. The standard deviation is also shown in each case.

FIG. 8a is a graph that shows the time for dissolution in phosphate buffered saline of predenatured solid protein solder strips prior to laser irradiation. The time for dissolution for each group of solder was calculated from the mean for ten specimens. The standard deviation is also shown in each case. Undenatured solder specimens were completely dissolved after 5 minutes of soaking in PBS. Solder specimens predenatured in a hot water bath at 75° C. took 150 minutes to dissolve. The time for dissolution of solder specimens predenatured at 100° C. and in glutaraldehyde was greatly increased (3.8 to 8.1 days). Predenaturation in a hot water bath at 75° C. was thus the optimal technique investigated, providing ample time for the surgical procedure to be performed. FIG. 8b is a graph that shows that after laser irradiation of the strips at 11.3 W/cm$^2$ for 40 s, no significant difference (p<0.05) was observed in the time for dissolution of solid protein solder strips previously undenatured or predenatured using any of the techniques described.

Figure 9:
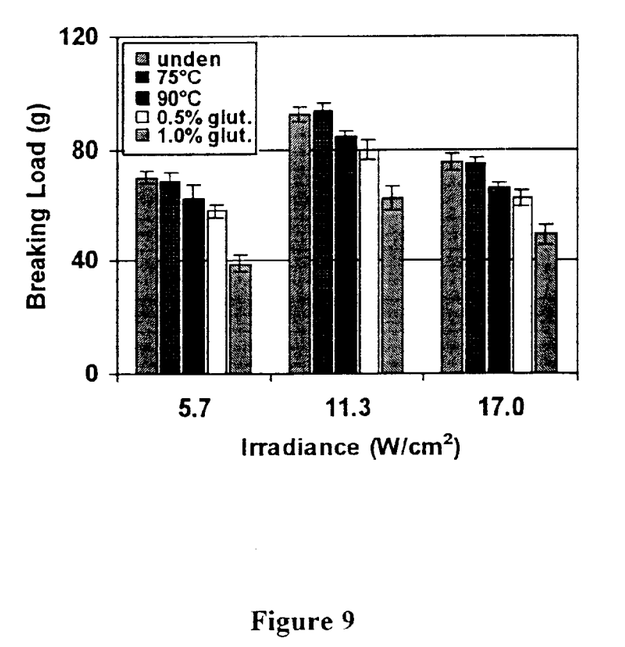
FIG. 9. A graph of the breaking load of tissue specimens repaired using the predenatured solid protein solder strips (60% BSA), as a function of laser irradiance. Each bar represents the mean and standard deviation for ten repairs.

FIG. 9 is a graph that shows the results of strength measurements made on tissue specimens successfully repaired using the predenatured solid protein solder strips, as a function of laser irradiance. The breaking load for each value of laser irradiance was calculated from the mean for ten repairs. The standard deviation is also shown in each case. There was no significant difference (p<0.05) between the strength of repairs formed using the undenatured solder and those specimens repaired using solder predenatured at 75° C. The strength of the repairs formed decreased with increased denaturation temperature (e.g., 100° C.). Strength was also reduced when the protein solders were predenatured in glutaraldehyde. The decrease in strength was attributed to the fact that glutaraldehyde is a known fixative, and some degree of fixation must have occurred in the albumin protein solder. Predenaturation of the solder at 75° C. is thus a feasible option for reducing the solubility of solder and to ensure that minimal mechanical alteration occurs that can weaken the solder-tissue repair during the surgical procedure.

The application of ICG-doped albumin protein solders to augment laser tissue repairs is shown to enhance edge co-optation, improve repair strength and to reduce thermal tissue injury. The moldable, absorption controllable and flexible nature of the novel solid protein solders presented greatly improves the clinical applicability of laser tissue solder repair.

REFERENCES

Bass L S, Moazami N, Pocsidio J, Oz M C, LoGerfo P and Treat M R, "Changes in Type I Collagen Following Laser Welding," Lasers Surg Med 12:500–505, 1992.

Bass L S, Libutti S K and Eaton A M, "New Solders for Laser Welding and Sealing," Lasers Surg Med Supp 5:63, 1993.

Bass L and Treat M, "Laser Tissue Welding: A Comprehensive Review of Current and Future Clinical Applications," Lasers Surg Med 17:315–349, 1995.

Chan E, Kovach I, Brown D, Welch A J, "Effects of Hydration on Laser Soldering," Proc SPIE 2970: 244–251, 1997.

Chikamatsu E, Sakurai T, Nishikimi N, Yano T and Nimura Y, "Comparison of Laser Vascular Welding, Interrupted Sutures, and Continuous Sutures in Growing Vascular Anastomoses," Lasers Surg Med 16:34–40, 1995.

Chow J W N and Flemming A F S, "Laser Assisted Microvascular Anastomosis: A Histological Study," Laser Med Sci 5:281–287, 1990.

Cikrit D F, Dalsing M C, Weinstein T S, Palmer K, Lalka S G and Unthank J L, "$CO_2$ Welded Venous Anastomosis: Enhancement of Weld Strength With Heterologous Fibrin Glue," Lasers Surg Med 10(6):584–590, 1990.

Dalsing M C, Packer C S, Kueppers P, Griffith S L and Davis T E, "Laser and Suture Anastomosis: Passive Compliance and Active Force Production," Lasers Surg Med 12:190–198, 1992.

Godlewski G, Prudhomme M and Tang J, "Applications and Mechanisms of Laser Tissue Welding in 1995. Review," Proc SPIE 2623:334–341, 1996.

Grubbs P E, Wang S, Corrado M, Basu S, Rose DM and Cunningham J N, "Enhancement of $CO_2$ Laser Microvascular Anastomosis by Fibrin Glue," J Surg Res 45:112–119, 1988.

How TV, Mechanical Properties of Arteries and Arterial Grafts. In: Hastings G W, ed. Cardiovascular Biomaterials. Great Britain: Springer-Verlag, 1–35, 1992.

Jain K K and Gorisch W, "Repair of Small Blood Vessels with the Neodymium-YAG Laser: A Preliminary Report," Surgery 85:684–688, 1979.

Kopchok G E, White R A, White G H, Fujitani R, Vlasak J, Dykhovsky L and Grundfest W S, "$CO_2$ and Argon Laser Vascular Welding: Acute Histological and Thermodynamic Comparison," Lasers Surg Med 8:584–588, 1988.

Kottke-Marchant K, Anderson J M, Umemura Y, Marchant R E, "Effect of Albumin Coating on the In Vitro Blood Compatibility of Dacro Arterial Prostheses," Biomaterials 10:147–155, 1989.

Krueger R R and Almquist E E, "Argon Laser Coagulation of Blood for Anastomosis of Small Vessels," Lasers Surg Med 5:55–60, 1985.

Lauto A, Poppas D P, Murrell G A C, "Solubility Study of Albumin Solders for Laser Tissue-Welding," Lasers Surg Med, 23:258–262, 1998.

Maragh H, Hawn R, Gould J and Terzis J, "Is Laser Nerve Repair Comparable to Microsuture Coaptation?," J Reconstr Microsurg 4:189–195, 1988.

McNally K M, Sorg B S, Chan E K, Welch A J, Dawes J M and Owen E R, "Optimal Parameters for Laser Tissue Soldering: Part I—Tensile Strength and Scanning Electron Microscopy Analysis," Lasers Surg Med 24:319–331, 1999a.

McNally K M, Sorg B S, Chan E K, Welch A J, Dawes J M and Owen E R, "Optimal Parameters for Laser Tissue Soldering: Part II—Premixed Versus Separate Dye/Solder Methods," Lasers Surg Med 1999b (accepted).

McNally K M, Sorg B S, Welch A J, Dawes J M and Owen E R, "Photothermal Effects of Laser Tissue Soldering," Phys Med Biol 44:983–1002, 1999c.

McNally K M, Sorg B S and Welch A J, "Novel Solid Solder Designs for Laser-Assisted Vascular Anastomosis," Lasers Surg Med Supp. 11:55, 1999d.

McNally K M, Sorg B S and Welch A J, "Solid Protein Solder-Doped Biodegradable Polymer Scaffolds for Laser-Assisted Tissue Repair," *Biomaterials* 1999 e (submitted).

McNally K M, Sorg B S and Welch A J, "Novel Solid Protein Solder Designs for Laser-Assisted Tissue Repair," *Lasers Surg Med* 1999f (submitted).

Mikos A G, Thorsen A J, Czerwonka L A, Bao Y, Langer R, Winslow D N and Vacanti J P, "Preparation and Characterization of Poly(L-Lactic Acid) Foams," *Polymer*, 35:1068–1077, 1994.

Pearce J and Thomsen S, "Rate Process Analysis of Thermal Damage," in Welch A J and van Gemert M J C, eds., *Optical-Thermal Response of Laser-Irradiated Tissue*, Plenum Press, New York, 1995.

Poppas D P, Choma T J, Rooke C T, Klioze S D and Schlossberg S M, "Preparation of Human Albumin Solder for Laser Tissue Welding," *Lasers Surg Med* 13:577–580, 1993.

Poppas D P, Schlossberg S M, Richmond I L, Gilbert D A and Devine C J, "Laser Welding in Urethral Surgery: Improved Results with a Protein Solder," *J Urol* 139:415–417, 1988.

Rosenberg N, Gaughran E R L, Henderson J, Lord G H, Douglas J F, "The Use of Segmental Arterial Implants Prepared by Enzymatic Modification of Heterologous Blood Vessels," *Surgical Forum* 6:242–246, 1982.

Schober R, Ulrich F, Sander T, Durselen H and Hessel S, "Laser Induced Alteration of Collagen Substructure Allows Microsurgical Tissue Welding," *Science* 232:1421–1422, 1986.

Thomsen S, Chan E, Stubig I, Menovsky T and Welch A J, "Importance of Wound Stabilization in Early Wound Healing of Laser Skin Welds," *Proc SPIE* 2395, 1995.

Thomsen S, Mueller J, Serure A, "Pathology of Rat Femoral Arteries Exposed to a Low-Energy $CO_2$ Laser Beam," *Lab Invest* 52:68A, 1985.

Wake M C, Gupta P K and Mikos A G, "Fabrication of Pliable Biodegradable Polymer Foams to Engineer Soft Tissues," *Cell Transplantation*, 5(4):465–473, 1996.

Wang S, Grubbs P E, Basu S, Robertazzi R R, Thomsen S, Rose D M, Jacobwitz I J and Cunningham J N, "Effect of Blood Bonding on Bursting Strength of Laser-Assisted Microvascular Anastomosis," *Microsurgery* 9:10–13, 1988.

Werker P M N and Kon M K, "Review of Facilitated Approaches to Vascular Anastomosis Surgery," *Ann Thor Surg* 63:S122–127, 1997.

What is claimed is:

1. A composition suitable for the repair of separated biological tissue comprising:

a solid biodegradable polymeric material chosen from the group consisting of poly(L-lactic acid) (PLA), poly (glycolic acid), poly(L-lactic-co-glycolic acid) (PGA), poly($\epsilon$-caprolactone) (PLGA), polyortho esters, polyanhydrides or combinations thereof;

a weldable material impregnated on the solid biodegradable polymeric material; and a chromophoric dye having a concentration gradient across the thickness of the biodegradable polymeric material.

2. The composition of claim 1, wherein the solid biodegradable polymeric material comprises a co-polymer of polylactic and polyglycolic acid (PLGA) where the weight ratio can vary between 0 and 100 percent.

3. The composition of claim 1, wherein the solid polymeric biodegradable material comprises a biologically compatible salt whose particle size alters the porosity of the polymeric biodegradable material.

4. The composition of claim 1, wherein the weldable material comprises a protein solder.

5. The composition of claim 4, wherein the protein solder has been denatured.

6. The composition of claim 4, wherein the protein solder comprises albumin protein solder.

7. The composition of claim 1, wherein the chromophoric dye comprises indocyanine green dye.

8. The composition of claim 1, wherein the chromophoric dye comprises carbon black.

9. The composition of claim 1, wherein the biodegradable polymeric material comprises:

a co-polymer of polylactic acid and polyglycolic acid (PLGA);

the weldable material comprises a protein solder, wherein the protein solder further comprises albumin; and the chromophoric dye comprises indocyanine green.

10. The composition of claim 1, wherein:

the biodegradable polymeric material comprises a co-polymer of polylactic acid and polyglycolic acid (PLGA) in which the ratio of polylactic acid to polyglycolic acid is 85 weight percent to 15 weight percent;

the weldable material comprises a protein solder, wherein the protein solder further comprises albumin; and the chromophoric dye comprises indocyanine green.

11. The composition of claim 1, further comprising one or more wound healing agents.

12. A method of joining separated biological tissue comprising the steps of:

forming a solid biodegradable polymeric material chosen from the group consisting of poly(L-lactic acid) (PLA), poly(glycolic acid) (PGA), poly(L-lactic-co-glycolic acid) PLGA, poly($\epsilon$-caprolactone), polyortho esters, polyanhydrides or combinations thereof;

impregnating the solid biodegradable material with a weldable material; and adding a chromophoric dye to the solid biodegradable polymeric material wherein the chromophoric dye has a concentration gradient across the thickness of the biodegradable polymeric material.

13. The method of claim 12, further comprising the steps of:

identifying a tissue in need of repair;

placing the solid biodegradable polymeric material on the tissue; and exposing the solid biodegradable polymeric material to laser light.

14. The method of claim 13, wherein the laser light wavelength matches absorption peaks in the absorption spectrum of the chromophoric dye.

15. A method for forming a solid biodegradable polymeric material for biological tissue repair comprising the steps of:

forming first and second weldable biodegradable polymeric material patches having a conentration gradient of chromophoric dye wherein the biodegradable material patches are chosen from the group consisting of poly(L-lactic acid) (PLA), poly(glycolic acid) (PGA), poly(L-lactic-co-glycolic acid) PLGA, poly($\epsilon$-caprolactone), polyortho esters, polyanhydrides or combinations thereof;

pressing the patches of treated biodegradable polymer together to form a single unit; and exposing the solid biodegradable polymeric material patches to laser light.

16. The method of claim 15, wherein the porosity of the biodegradable polymeric material of said first and second patch is different.

17. The method of claim 15, wherein the patches are further held using sutures, staples, or other means of physically joining tissue.

18. The method of claim 15, wherein the laser light is provided by a GaAlAs semiconductor diode laser with output at 805 nm.

19. The method of claim 15, wherein the laser light is provided by a GaAlAs semiconductor diode laser with output at 805 nm and a nominal power output of 5 W.

20. A composition suitable for establishing hemostasis of bleeding tissue comprising:

- a solid biodegrable polymeric material chosen from the group consisting of poly(L-lactic acid) (PLA), poly (glycolic acid) (PGA), poly(L-lactic-co-glycolic acid) PLGA, poly($\epsilon$caprolactone), polyortho esters, polyanhydrides or combinations thereof;
- a weldable material impregnated on a solid biodegradable polymeric material; and
- a chromophoric dye having a concentration gradient across the thickness of the biodegradable polymeric material.

21. The composition of claim 20, further comprising a chromophoric dye.

* * * * *

UNITED STATES PATENT AND TRADEMARK OFFICE
CERTIFICATE OF CORRECTION

PATENT NO.    : 6,391,049 B1
DATED         : May 21, 2002
INVENTOR(S)   : Karen N. McNally, Brian S. Sorg and Ashley J. Welch It is certified that error appears in the above-identified patent and that said Letters Patent is hereby corrected as shown below:

<u>Title page,</u>
Item [74], *Attorney, Agent, or Firm,* please delete "Santa E. Warren, Jr.; Edwin S. Flores; Gardere Wynne Sewell LLP" and insert -- Sanford E. Warren, Jr.; Edwin S. Flores; Gardere Wynne Sewell LLP --.

Signed and Sealed this

Eighteenth Day of March, 2003

JAMES E. ROGAN
*Director of the United States Patent and Trademark Office*